United States Patent
Seiffert et al.

(10) Patent No.: US 12,296,070 B2
(45) Date of Patent: May 13, 2025

(54) ANTIBACTERIAL IMPLANT COATING COMPOSITION, METHOD OF IMPLANT COATING AND ANTIBACTERIAL COATED IMPLANT

(71) Applicant: GEBR. BRASSELER GMBH & CO. KG, Lemgo (DE)

(72) Inventors: Anne Seiffert, Braunschweig (DE); Henning Menzel, Lehrte (DE); Michael Küllmer, Lemgo (DE); Hans-Christoph Schwarz, Bad Salzuflen (DE); Meike Stiesch, Hannover (DE); Andreas Winkel, Hannover (DE); Jasmin Grischke, Hannover (DE)

(73) Assignee: GEBR. BRASSELER GMBH & CO. KG, Lemgo (DE)

( * ) Notice: Subject to any disclaimer, the term of this patent is extended or adjusted under 35 U.S.C. 154(b) by 5 days.

(21) Appl. No.: 17/714,594

(22) Filed: Apr. 6, 2022

(65) Prior Publication Data
US 2022/0331494 A1   Oct. 20, 2022

(30) Foreign Application Priority Data

Apr. 9, 2021  (DE) .......................... 102021108936.0

(51) Int. Cl.
*A61L 27/54*  (2006.01)
*A61L 27/34*  (2006.01)
*C08L 33/02*  (2006.01)

(52) U.S. Cl.
CPC .............. *A61L 27/54* (2013.01); *A61L 27/34* (2013.01); *C08L 33/02* (2013.01); *A61L 2420/02* (2013.01)

(58) Field of Classification Search
None
See application file for complete search history.

(56) References Cited

U.S. PATENT DOCUMENTS

2013/0252021 A1 * 9/2013 Neumann ............... A61L 27/54
                                                             106/18.32
2017/0096565 A1 * 4/2017 Menzel ................... A61L 27/54

FOREIGN PATENT DOCUMENTS

EP  1707601 A1 * 10/2006  .............. A61L 2/16
EP  3153186 A1   4/2017

OTHER PUBLICATIONS

European Search Report dated Aug. 29, 2022 from counterpart European Patent Application No. 22164499.0.

* cited by examiner

*Primary Examiner* — Carlos A Azpuru
*Assistant Examiner* — Casey S Hagopian
(74) *Attorney, Agent, or Firm* — SHUTTLEWORTH & INGERSOLL, PLC; Timothy J. Klima

(57) ABSTRACT

The invention relates to an antibacterial implant coating composition including a graft copolymer comprising a (meth)acrylic acid-based backbone and phosphonate side chains, wherein at least one phosphonate side chain is linked to a guanidine oligomer through an N—P bond.

18 Claims, 1 Drawing Sheet

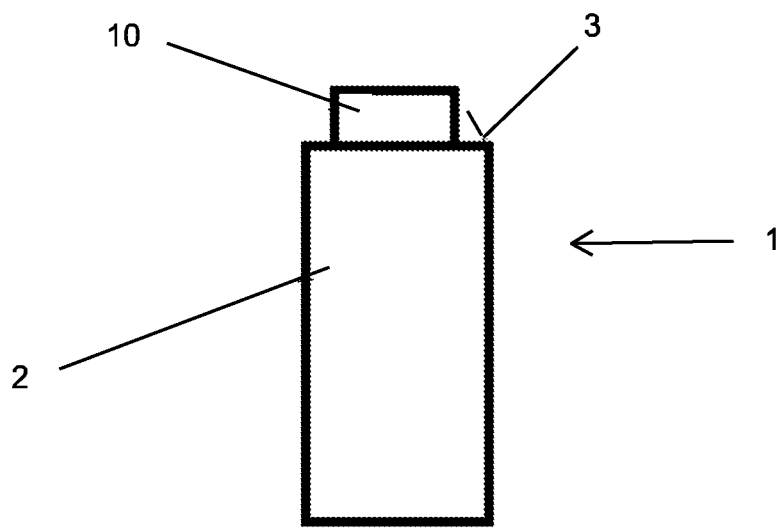

ANTIBACTERIAL IMPLANT COATING COMPOSITION, METHOD OF IMPLANT COATING AND ANTIBACTERIAL COATED IMPLANT

This application claims priority to German Patent Application DE102021108936.0 filed Apr. 9, 2021, the entirety of which is incorporated by reference herein.

The invention relates to an antibacterial implant coating composition having excellent antibacterial activity and implant adhesion. In addition, the present invention also relates to a method for coating an implant and an antibacterial coated implant.

Implants are used in many medical disciplines for reconstructing organ and tissue functions. They are made of artificial materials to which bacteria can adhere and organize themselves into complex biofilm communities. The resulting inflammatory reactions and associated progressive destructive processes occurring in the adjacent tissue cause loss of function in implant and considerable impairment of the patient. Especially in dentistry, peri-implant infections with a prevalence of 30% are of great clinical importance. Due to high resistance of bacterial biofilms to chemical therapeutics, biofilm removal in dentistry is predominantly done mechanically, resulting in incomplete access to many areas of the dental implant caused by its complex geometry.

The issue of implant-associated infections is currently being addressed by coating the implant with silver. The silver coating prevents bacterial adhesion as well as adhesion of endogenous cells, and therefore is not selective. Antibacterial polymers applied to implant materials is another new approach. However, polymers developed to date either lack cell compatibility or do not exhibit sufficient antibacterial activity. Another issue resides in the safe and technically feasible application of the polymers to the surface.

Based on this prior art, it is the object of the present invention to provide an antibacterial implant coating composition that is easily to be to applied, adheres well to the implant, and having excellent cell compatibility with, simultaneously, good antibacterial activity. Another object of the present invention is to provide a method for coating an implant with an antibacterial coating that produces a uniformly covering coating that adheres well to the implant, while avoiding high technical expenditure and still is simple in realization. In addition, it is an object of the present invention to disclose an antibacterial coated implant that is characterized by excellent antibacterial functionality while simultaneously having high cell compatibility.

These objects will be solved by the features of the independent claims. The dependent claims relate to advantageous further embodiments.

Accordingly, the object will be solved by an antibacterial implant coating composition comprising a specific graft copolymer, the graft copolymer comprising a backbone based on (meth)acrylic acid.

By generally "(meth)acrylic acid-based backbone" and the like, according to the present invention, it is understood both a propenoic acid-based compound, i.e., acrylic acid, and a 2-methylpropenoic acid-based compound, i.e., methacrylic acid, namely, according to the above example, an "acrylic acid-based backbone" and an "methacrylic acid-based backbone". For the sake of simplicity, the abbreviation "(meth)acrylic acid . . . " is used in the following description as a substitute for "acrylic acid . . . and "methacrylic acid . . . ".

Phosphonate side chains are attached to the (meth)acrylic acid-based backbone. In other words, a poly(meth)acrylic acid backbone is present in the graft copolymer, wherein the phosphonate side chains are linked to the acid groups or ester groups of the poly(meth)acrylic acid backbone. In this case, the phosphonate side chains are not required to be directly reacted with the acid groups or ester groups, but a divalent linking group, such as especially an alkylene group, which especially comprises 1 to 8 carbon atoms and preferably 1 to 4 carbon atoms, may as well be present between the phosphorus atom of the phosphonate side chains and the single-bonded oxygen of the carboxyl group or ester group of the poly(meth)acrylic acid backbone. However, the divalent linking group does not affect the antibacterial functionality of the graft copolymer.

Rather, the antibacterial functionality of the graft copolymer emanates from a guanidine oligomer linked to the phosphonate side chain. According to the present invention, guanidine oligomers are derivatives of oligoguanidines that can be synthesized, especially by reacting diamines with guanidine hydrochloride. Oligoguanidines and polyguanidines are known for combating microorganisms and are often used in disinfectants, detergents and cleaning agents or cosmetics. Due to their high water solubility, they are not suitable for coating implants in the form previously used.

In the graft copolymer used according to the invention, at least one phosphonate side chain is linked to a guanidine oligomer by an N—P bond. The N—P bond is a covalent bond between a nitrogen atom of the guanidine oligomer and the phosphorus atom of a phosphonate side chain. The resulting linking group especially is a phosphonamidate group. This means that preferably a primary amine group is reacted with the phosphonate group, resulting in the direct and covalent N—P bond described above.

In the graft copolymer used according to the invention, one or more phosphonate groups may be reacted and linked to one or more guanidine oligomers. The higher the proportion of guanidine oligomer residues, the higher the antibacterial protective effect that the antibacterial implant coating composition can exert. However, an antibacterial effect is obtained even at very low levels of guanidine oligomer in the graft copolymer and, as it is shown, can be increased by increasing the proportion of N—P-linked guanidine oligomer groups.

In the graft copolymer used for the antibacterial implant coating composition, the (meth)acrylic acid-based backbone serves both to provide stability to the implant coating composition, and to provide phosphonate side chains in sufficient numbers. The phosphonate side chains provide anchoring function to the graft copolymer for bonding to common implant materials such as titanium, stainless steel, zirconium, tantalum, zirconia, PEEK and the like. Thus, the implant coating composition according to the invention is self-bonding. It does not require any additional adhesive component. This facilitates an application of the implant coating composition on the implant and enables coatings even on geometrically complex implant surfaces.

The antibacterial effect of the implant coating composition is achieved by the covalently bonded guanidine oligomer residue(s), which are no longer water-soluble due to the covalent bond, thus permanently remaining in place following application to an implant, developing their antibacterial effect.

The implant coating composition according to the invention is thus characterized by a high degree of functionality and still having a simple structure, as it essentially contains the graft copolymer described above as the functional component. The antibacterial implant coating composition thus is easy to be processed and especially to be uniformly applied in the desired layer thickness, it adheres well and durably to the implant, and is highly compatible with cells while simultaneously having an excellent antibacterial effect.

To optimize the antibacterial properties of the implant coating composition while maintaining excellent adhesion to an implant, a proportion of phosphonate side chains linked to a guanidine oligomer by a (covalent) N—P bond, based on the total proportion of phosphonate side groups in mol %, is preferably 0.8 to 6 mol % and especially is 0.9 to 5 mol %. Even very low proportions of phosphonate side chains covalently linked to a guanidine oligomer of 0.8 mol % will achieve a particularly good and durable antibacterial effect owing to the high antibacterial functionality of guanidine oligomers. The remaining phosphonate side chains, which are not linked to a guanidine oligomer, can preferably serve to bind to the implant. Thus, good balance is achieved between sufficient adhesion to an implant and very good antibacterial activity while maintaining high cell compatibility. A mol % fraction of 0.8 to 6 mol % of phosphonate side chains linked to a guanidine oligomer by an N—P bond, as disclosed above, approximately corresponds to a mass fraction of 4 to 30 mass %, based on the total mass of all phosphonate side chains in the graft copolymer.

According to another advantageous further embodiment, the phosphonate side chains which are not linked to the guanidine oligomer are not hydrolyzed, and are partially hydrolyzed so as to form hemi phosphonic acid residues, or are fully hydrolyzed so as to form phosphonic acid residues. This essentially does not affect the functionality of the graft copolymer. At most, water dispersibility of the graft copolymer can be improved by a higher degree of hydrolysis of the phosphonate side chains.

Preferably, a proportion of partially hydrolyzed and fully hydrolyzed phosphonate side groups, based on the total proportion of phosphonate side groups in mol %, is 5 to 30 mol % and especially 7 to 20 mol %. This allows very good dispersing properties to be achieved in polar solvents. A mol % fraction of 5 to 30 mol % of partially hydrolyzed and fully hydrolyzed phosphonate side groups, based on the total fraction of phosphonate side groups, in this case corresponds to about 6 to 25 mass %, based on the total mass of all phosphonate side chains in the graft copolymer.

Further advantageously, the graft copolymer used according to the invention has a molecular weight (Mw) which satisfies the following equation:

$$5\ kDa < Mw < 40\ kDa.$$

The molecular weight can be calculated from DOSY NMR data. A molecular weight in the range indicated has the advantage in that, on the one hand, it is high enough to allow a film of the antibacterial implant coating composition having good adherence on an implant to be realized, and, on the other hand, is low enough to provide good processability, especially high dispersibility in solvents, so that the antibacterial implant coating composition can uniformly be applied in desired film thickness.

Preferably, the guanidine oligomer is at least one compound represented by the following formulae, since these guanidine oligomers are characterized by very good connectivity to the phosphonate side chains and high antibacterial activity. Only one specific guanidine oligomer may be used in the graft copolymer, or a combination of two or more guanidine oligomers represented by the following formulas may be used:

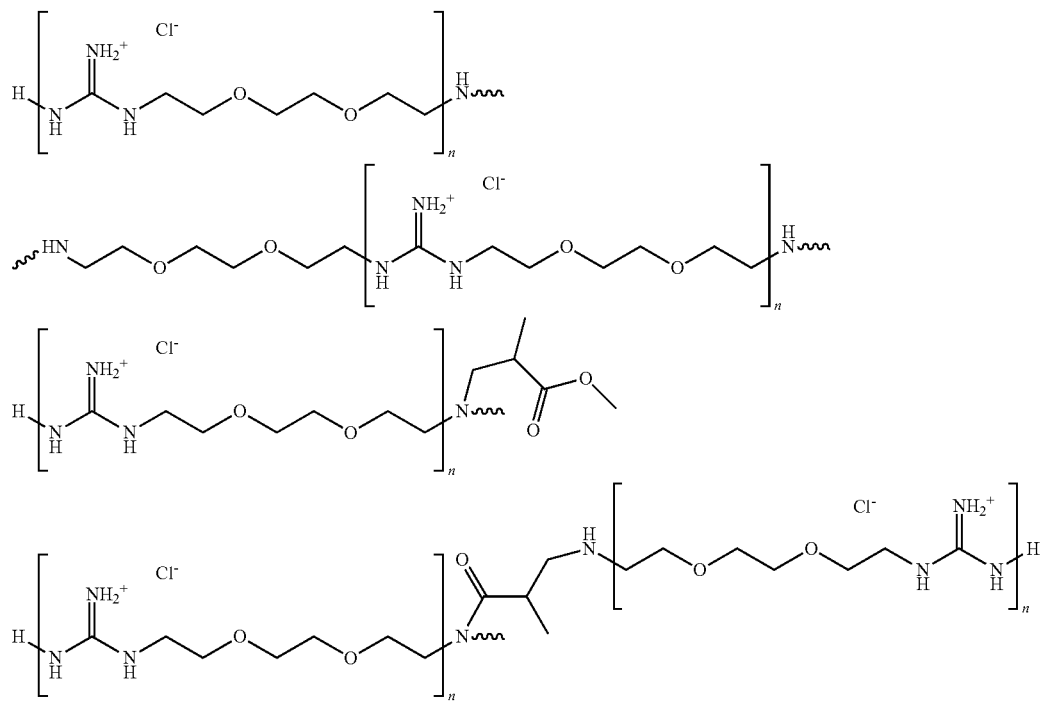

In the formulas disclosed above, each one of n denotes an integer from 2 to 10, preferably from 3 to 6, and especially 5, and an undulation, "~", denotes any preferred bonding position of the corresponding nitrogen to the phosphorus atom of a phosphonate side chain. As shown in the above formulas, the guanidine oligomers in some cases have several primary and also secondary amine groups which basically are suitable for reacting with a phosphorus atom of a phosphonate side chain. Preferably, however, a reaction occurs at that nitrogen atom which is marked with an undulation, "~".

Also in light of a very good dispersibility of the graft copolymer, the molecular weight of the guanidine oligomer is preferably 800 to 1300 g/mol. In calculating the molecular weight of the guanidine oligomer, the guanidine oligomer residue is considered as bonded to the phosphorus atom of the phosphonate side chain.

Further advantageously, the graft copolymer comprises the following structural unit:

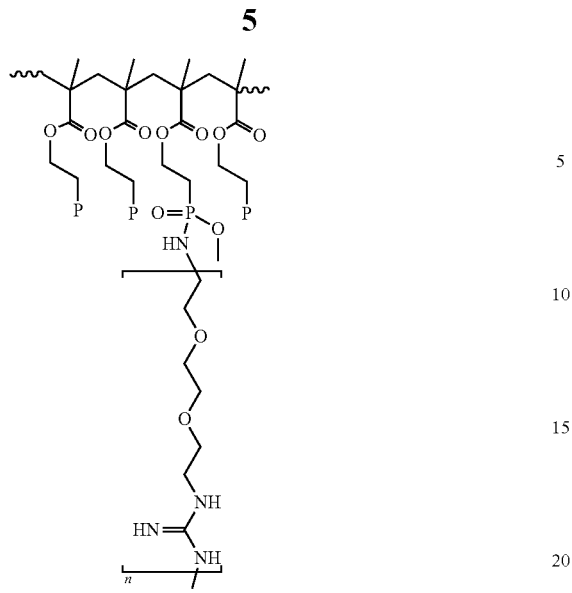

wherein each one of P represents a phosphonate group which may be unhydrolyzed, partially hydrolyzed or fully hydrolyzed, and wherein n represents an integer from 2 to 10, preferably from 3 to 6, and is especially 5. An undulation in the (meth)acrylic acid based backbone represents a binding position to another (meth)acrylic acid units. If the graft copolymer contains the structural unit above, a particularly excellent antibacterial effect, excellent adhesion to the implant and at the same time excellent cell compatibility will be obtained.

The above properties can further be improved if, as disclosed according to another embodiment, the graft copolymer comprises at least one of the following structural units:

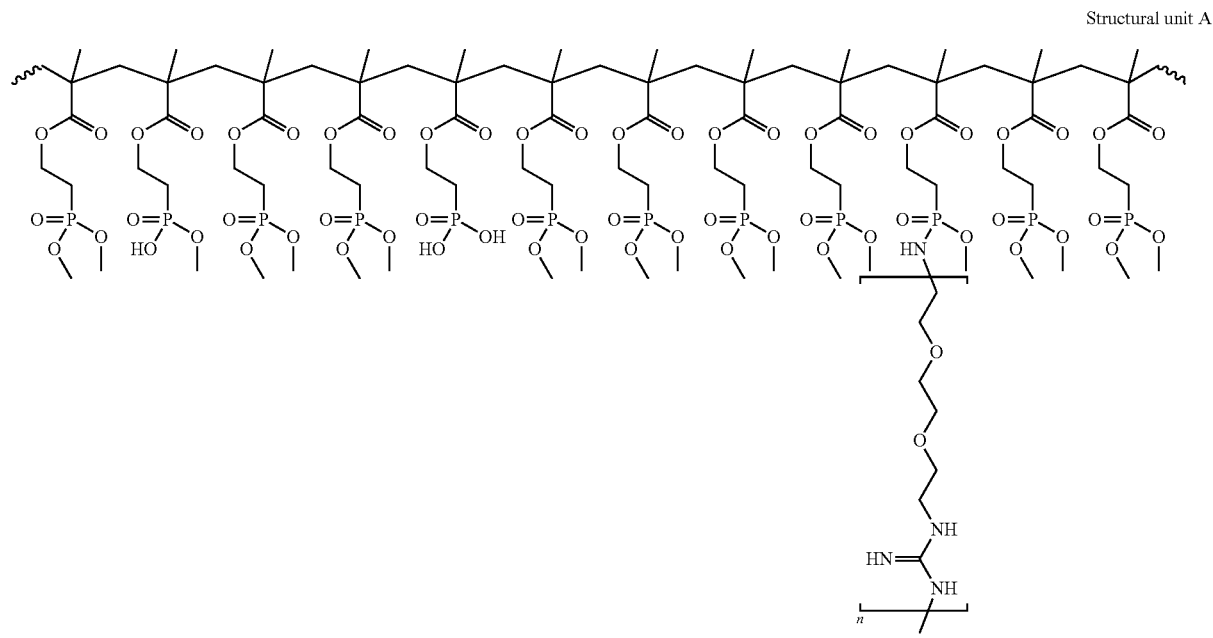

Structural unit A

-continued

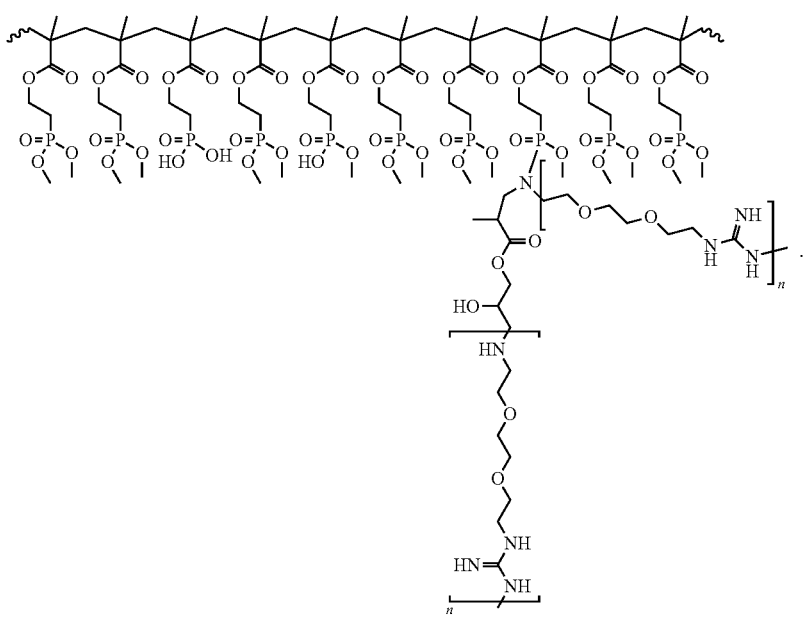

Structural unit B

In the structural units disclosed, each one of n is an integer from 2 to 10, preferably from 3 to 6, and is especially 5. An undulation in the (meth)acrylic acid-based backbone represents a binding position to other (meth)acrylic acid units.

Preferably, the antibacterial implant coating composition contains only the graft copolymer disclosed above and, optionally, unreacted or incompletely reacted reactants resulting from the preparation of the graft copolymer. This constitutes the functional component of the antibacterial implant coating composition. As a result, the implant coating composition is highly durable and storable without loss of efficacy. However, to apply the antibacterial implant coating composition to an implant, it may further comprise a solvent or dispersant, such as water, ethanol, methanol, or any mixtures thereof. In the aforementioned solvents, the graft copolymer is highly soluble or at least dispersible and is therefore easy to process and to apply.

The antibacterial implant coating composition may furthermore contain other components, if necessary, but they do not impair the effectiveness of the graft copolymer.

Also disclosed according to the invention is a method for coating an implant with an antibacterial coating. For this purpose, the implant coating composition described above is dissolved or dispersed in a solvent, in one processing step. Provided that a solution of the implant coating composition is obtained, the solution may be colloidal. The solvent may, for example, be water, ethanol or methanol, or any mixtures thereof. Next, an implant is provided, which should be degreased for further processing. Degreasing can be carried out, for example, by cleaning with solvents such as acetone, dichloromethane, methanol and the like, or by use of plasma cleaning. If necessary, after drying, the dissolved or dispersed implant coating composition is then applied to the implant. The fact that the implant coating composition is in the form of a solution or dispersion means that many simple, conventional application procedures may be used, keeping the technical expenditure of the method low. It also simplifies application to geometrically complex surfaces. Finally, the implant coating composition is bonded to the implant. This is carried out by exposing the implant to temperatures between 50 and 200° C., e.g. in a drying oven or in a suitable furnace. The bonding step causes the implant coating composition to be coated onto the surface of the implant and covalently bonds to the implant through the phosphonate groups. The binding force of the bond between the implant surface and the implant coating composition is high due to the high proportion of phosphonate side chains. Application of an adhesive may therefore be omitted. The method provides an implant having permanently high antimicrobial efficacy while simultaneously having very good cell compatibility without the need of high technical expenditure.

The advantages, advantageous further embodiments and embodiments set forth above for the antimicrobial implant coating composition also apply to the method according to the invention for coating an implant using an antibacterial coating.

To purify the coating, a washing step and a drying step may follow the binding of the implant coating composition.

Further, prior to coating, the implant may undergo customary preparation steps, such as polishing the surface to obtain a desired surface roughness, for example, a surface roughness of 0.013 μm or below.

Another advantageous further development of the method resides in that application of the implant coating composition solution is carried out by spin coating (especially for planar substrates), a dipping or spraying method. This simplifies process control thus resulting in a coating having particularly uniform layer thickness.

Excellent reactivity of the implant coating composition with the implant surface resulting in formation of a uniform layer thickness is advantageously obtained in that concentration of the implant coating composition in the solvent is 2 to 20 mg/ml and especially 8 to 12 mg/ml.

Still according to the invention, an antimicrobial coated implant is also described. The antimicrobial coated implant comprises a coating formed from the implant coating composition described above. In this regard, the coating may be prepared according to the method described above, for coating an implant with an antibacterial coating. The implant according to the invention is formed of titanium, zirconium, tantalum, stainless steel, zirconium oxide or PEEK and has an average layer thickness of the antimicrobial coating of 5 to 50 nm and especially of 15 to 25 nm. The coating thickness is determined by ellipsometry. The coating thickness obtained by the method according to the invention in the implant according to the invention is about 10 nm higher than that obtained by alternative manufacturing methods of a coating composition under otherwise identical conditions. This indicates that the chemical structure of the implant coating composition is not comparable to structures of conventional antibacterial coatings. Exemplary implants according to the invention include dental implants, implants for hip and knee endoprostheses, and cardiac pacemakers. Especially in tumor therapy, when immunosuppressed patients receive large implants, infection prophylaxis is of enormous importance. The present invention is particularly suitable for dental implants, which generically are in contact with the patient's oral cavity, which is subject to high bacterial load and is therefore exposed to a particular risk of infection.

EXAMPLE

The synthesis of a graft copolymer used in the antibacterial implant coating composition of the invention will be described below:

The synthesis was carried out in two steps. In the first step, 2,2'-(ethylenedioxy)diethylamine and guanidine hydrochloride were fused at 170° C. using a mechanical stirrer to obtain the oligomeric product poly-(2-(2-ethoxy)-ethoxyethyl-guanidine hydrochloride) (PEDBEG). The oligomeric guanidine comprised primary amines that undergo reactions as a functional group and are able to form covalent N—P bonds with phosphonate groups, as set forth in the next step.

In the second step, 2-(dimethoxyphosphoryl)ethyl methacrylate (DMMEP) was polymerized for 14 h at 60° C. in the presence of the PEDBEG oligomer obtained in the first step. 2,2'-Azobis(2-methylpropionitrile) served as the initiator. In this reaction, assembly of the poly(DMMEP) backbone and reaction of the phosphonate side chains with the PEDBEG occurred. The product of this reaction, in addition to pure PEDBEG and poly(2-(dimethoxyphosphoryl)ethyl methacrylate), represented a graft copolymer that contained PEDBEG bound through a phosphorus-nitrogen bond as a side group. Furthermore, the phosphonate groups were hemihydrolyzed or fully hydrolyzed to about 7-20 mol %.

In the following table, a percentage composition of phosphorus atoms in the corresponding groups is set forth for different batches of graft copolymer preparation:

| | Phosphonate | Phosphonamidate | Phosphonic acid | Hemi-phosphonic acid |
|---|---|---|---|---|
| Charge AS1 | 78.66% | 2.07% | 13.01% | 2.89% |
| Charge AS2 | 78.07% | 1.77% | 14.01% | 3.04% |
| Charge AS3 | 75.37% | 2.50% | 13.08% | 5.16% |
| Charge LF1 | 82.94% | 3.20% | 12.24% | 1.12% |

| | Phosphonate | Phosphonamidate | Phosphonic acid | Hemi-phosphonic acid |
|---|---|---|---|---|
| Average | 79% | 2.4% | 13% | 3.0% |
| From-to | 75-83% | 1.8-3.2% | 12-14% | 1-5% |
| Mass fraction* | 78 | 8% | 11% | 3% |

*of the corresponding structures calculated using the average value and assuming an average molecular weight of 537 g/mol for the PEDBEG oligomers used.

Further details, advantages and features of the present invention will arise from the following description of embodiments while reference will be made to the drawing, wherein:

FIG. 1 is a schematic representation of an implant coated with an antibacterial coating according to one embodiment of the invention.

FIG. 1 shows a detailed schematic representation of an implant 1 coated with an antibacterial coating 10 according to one embodiment of the invention. The antibacterial coated implant 1 comprises a base body 2 comprising, for example, titanium, zirconium, tantalum, stainless steel, zirconium oxide or PEEK. On a surface 3 of the base body 2, the antibacterial coating 10 is arranged with an average layer thickness S of 5 to 50 nm and especially 15 to 25 nm.

The antibacterial coating 10 is formed from an antibacterial implant coating composition comprising a graft copolymer having a (meth)acrylic acid-based backbone and phosphonate side chains, wherein at least one phosphonate side chain is linked to a guanidine oligomer through an N—P bond. At least one additional phosphonate side chain, which is not linked to a guanidine oligomer by an N—P bond, is bonded to the implant surface 3, thereby providing good adhesion of the graft copolymer to the base body 2.

The antibacterial coating 10 on the base body 2 of the implant was obtained as follows:

First, the implant coating composition described above was dissolved or dispersed in a solvent such as water, ethanol or methanol. Next, an implant to be coated was provided and degreased. Subsequently, the solution or dispersion of the implant coating composition was applied to the surface 3 of the base body 2 of the implant, e.g. by spin coating or using a dipping or spraying method, followed by bonding the implant coating composition to the implant under the action of temperatures in a range of 50 to 200° C., thereby forming the antibacterial coating 10 between the surface 3 of the implant 10 and the implant coating composition by establishing bonds between the surface 3 of the implant and the phosphonate side chains of the graft copolymer of the implant coating composition. Herein, a concentration of the implant coating composition in the solvent was 2 to 20 mg/ml.

The antibacterial coated implant 1 was characterized by having durable excellent antibacterial functionality resulting from the antibacterial coating 10 having high cell compatibility. Coating of the implant using the antibacterial coating 10 was carried out in a manner of uniformly covering and using technically conventional means.

In addition to the foregoing written description of the invention, explicit reference herein will be made to the graphic representation of the invention in FIG. 1 for supplementary disclosure thereof.

LIST OF REFERENCE NUMBERS 1 antibacterial coated implant
2 base body
3 surface
10 antibacterial coating

The invention claimed is:

1. An antibacterial implant coating composition comprising a graft copolymer comprising:
   a (meth)acrylic acid-based backbone and
   phosphonate side chains,
wherein at least one of the phosphonate side chains is linked to a guanidine oligomer through a N—P bond;
wherein the guanidine oligomer formed by reacting a diamine with guanidine hydrochloride.

2. The antibacterial implant coating composition according to claim 1, wherein a proportion of phosphonate side chains linked to a guanidine oligomer through a N—P bond is 0.8 to 6 mol % based on the total proportion of phosphonate side groups in mol %.

3. The antibacterial implant coating composition according to claim 2, wherein a proportion of phosphonate side chains linked to a guanidine oligomer through a N—P bond is 0.9 to 5 mol %, based on the total proportion of phosphonate side groups in mol %.

4. The antibacterial implant coating composition according to claim 1, wherein the phosphonate side chains not linked to the guanidine oligomer are not hydrolyzed, partially hydrolyzed or fully hydrolyzed.

5. The antibacterial implant coating composition according to claim 4, wherein a proportion of partially hydrolyzed and fully hydrolyzed phosphonate side groups is 5 to 30 mol % based on the total proportion of phosphonate side groups in mol %.

6. The antibacterial implant coating composition according to claim 5, wherein a proportion of partially hydrolyzed and fully hydrolyzed phosphonate side groups is 7 to 20 mol % based on the total proportion of phosphonate side groups in mol %.

7. The antibacterial implant coating composition according to claim 1, wherein the molecular weight of the graft copolymer (Mw) satisfies the following equation:

$$5\ kDa < Mw < 40\ kDa.$$

8. The antibacterial implant coating composition according to claim 1, wherein the guanidine oligomer is at least one compound represented by the following formulas:

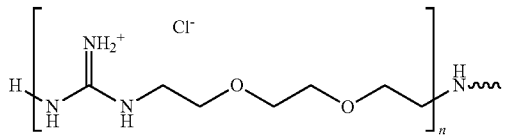

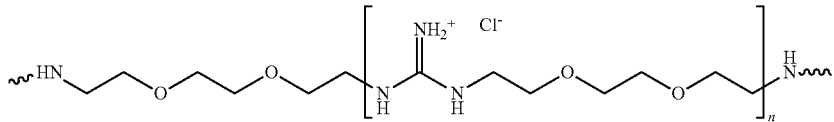

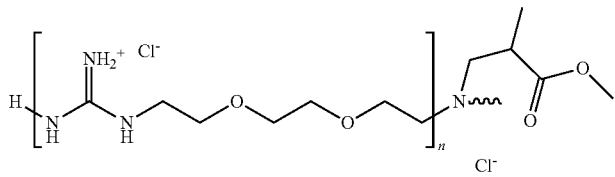

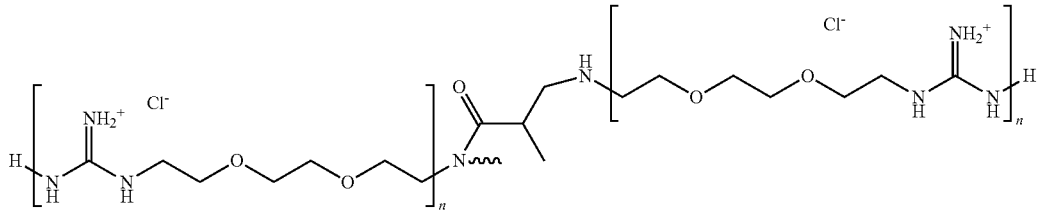

wherein each one of n is an integer from 2 to 10, and wherein "~" represents a bonding position to the phosphorus atom of a phosphonate side chain.

9. The antibacterial implant coating composition according to claim 1, wherein the molecular weight of the guanidine oligomer is 800 to 1300 g/mol.

10. The antibacterial implant coating composition according to claim 1, wherein the graft copolymer comprises the following structural unit:

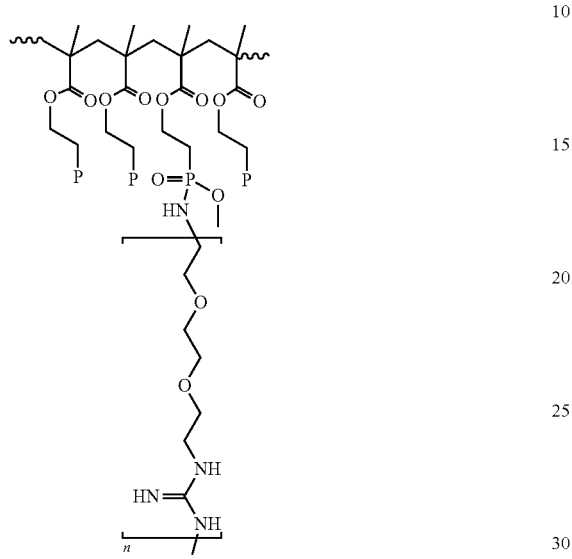

wherein each one of P represents a phosphonate group, wherein n represents an integer from 2 to 10, and wherein an undulation in the (meth)acrylic acid-based backbone represents a bonding position to an adjacent (meth)acrylic acid moiety.

11. The antibacterial implant coating composition of claim 10, wherein n represents an integer from 3 to 6.

12. The antibacterial implant coating composition according to claim 1, wherein the graft copolymer comprises at least one of the following structural units:

Structural unit A

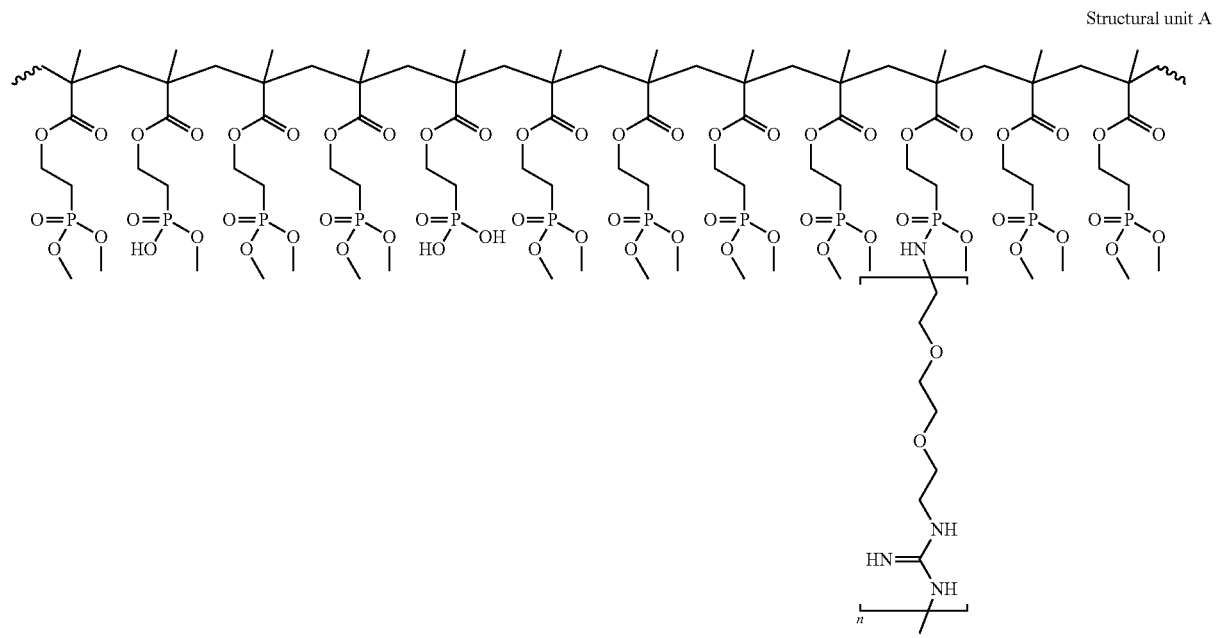

-continued

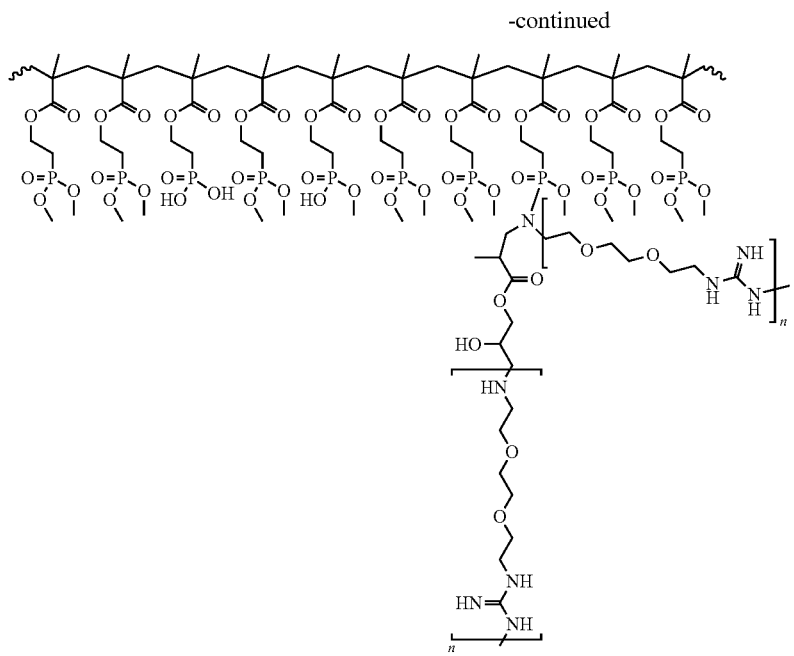

Structural unit B wherein each one of n represents an integer from 2 to 10, and wherein an undulation in the (meth)acrylic acid-based backbone represents a binding position to an adjacent (meth)acrylic acid moiety.

13. The antibacterial implant coating composition according to claim 12, wherein n represents an integer from 3 to 6.

14. The antibacterial implant coating composition according to claim 1, further comprising water.

15. The antibacterial implant coating composition according claim 14, wherein the graft copolymer comprises the following structural unit:

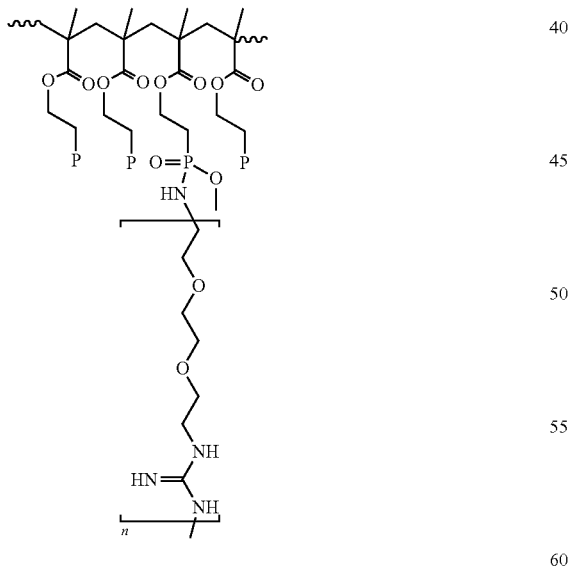

wherein each on of P represents a phosphonate group, wherein n represents an integer from 2 to 10, and wherein an undulation in the (meth)acrylic acid-based backbone represents a bonding position to an adjacent (meth)acrylic acid moiety.

16. The antibacterial implant coating composition of claim 15, wherein n represents an integer from 3 to 6.

17. The antibacterial implant coating composition of claim 14, wherein the graft copolymer comprises at least one of the following structures:

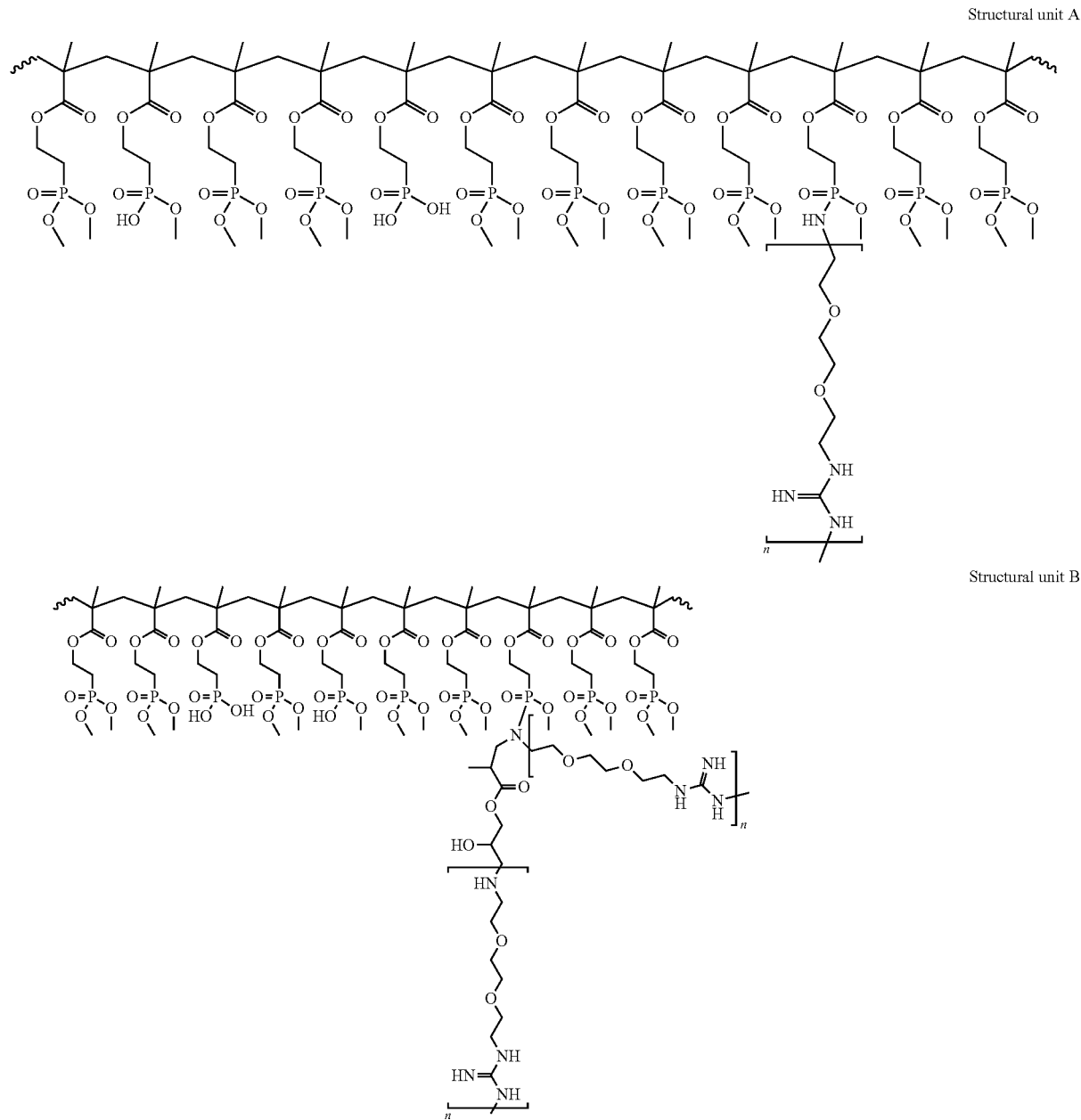

Structural unit A

Structural unit B wherein each one of n represents an integer from 2 to 10, and wherein an undulation in the (meth)acrylic acid-based backbone represents a binding position to an adjacent (meth)acrylic acid moiety.

18. The antibacterial implant coating composition according to claim 17, wherein n represents an integer from 3 to 6.

* * * * *